United States Patent
Merhi et al.

(10) Patent No.: US 10,850,134 B2
(45) Date of Patent: *Dec. 1, 2020

(54) METHOD AND KIT FOR HOME CONTROLLED OVARIAN STIMULATION FOR IN VITRO FERTILIZATION

(71) Applicants: Zaher Merhi, New Rochelle, NY (US); John Zhang, New York, NY (US)

(72) Inventors: Zaher Merhi, New Rochelle, NY (US); John Zhang, New York, NY (US)

(73) Assignees: Zaher Merhi, New Rochelle, NY (US); John Zhang, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/867,308

(22) Filed: May 5, 2020

(65) Prior Publication Data
US 2020/0346047 A1 Nov. 5, 2020

Related U.S. Application Data

(63) Continuation of application No. 16/674,565, filed on Nov. 5, 2019, now Pat. No. 10,695,589.

(60) Provisional application No. 62/841,571, filed on May 1, 2019.

(51) Int. Cl.
| | |
|---|---|
| *A61P 15/08* | (2006.01) |
| *A61B 10/00* | (2006.01) |
| *A61K 9/00* | (2006.01) |
| *A61B 5/00* | (2006.01) |
| *A61K 31/4196* | (2006.01) |
| *A61K 38/09* | (2006.01) |
| *A61K 31/135* | (2006.01) |
| *A61K 31/505* | (2006.01) |

(52) U.S. Cl.
CPC .......... *A61P 15/08* (2018.01); *A61B 5/4839* (2013.01); *A61B 10/0012* (2013.01); *A61K 9/0034* (2013.01); *A61K 9/0043* (2013.01); *A61K 9/0053* (2013.01); *A61K 31/135* (2013.01); *A61K 31/4196* (2013.01); *A61K 31/505* (2013.01); *A61K 38/09* (2013.01)

(58) Field of Classification Search
CPC ... A61B 10/0012; A61B 5/4839; A61P 15/08; A61K 9/0034; A61K 9/0043; A61K 9/0053; A61K 31/135; A61K 31/4196; A61K 31/505; A61K 38/09
See application file for complete search history.

(56) References Cited

U.S. PATENT DOCUMENTS

| | | | | |
|---|---|---|---|---|
| 2015/0272622 A1* | 10/2015 | Carson | ............ | A61K 31/58 600/34 |
| 2015/0335700 A1* | 11/2015 | Carson | ............ | A61K 38/08 514/10.4 |
| 2020/0046797 A1* | 2/2020 | Rajasekhar | ............ | A61P 15/08 |

OTHER PUBLICATIONS

Struthers et al. "Suppression of Gonadotropins and Estradiol in Premenopausal Women by Oral Administration of the Nonpeptide GnRH Antagonist Elagolix", J Clin Endocrinol Metab. Feb. 2009; 94(2): 545-551. First published online Nov. 25, 2008. doi: 10.1210/jc.2008-1695 (Year: 2008).*

* cited by examiner

*Primary Examiner* — Kaylee R Wilson
(74) *Attorney, Agent, or Firm* — Leason Ellis LLP

(57) ABSTRACT

A home controlled ovarian hyperstimulation method for in vitro fertilization (IVF) or egg freezing and a home IVF kit are described herein.

9 Claims, 3 Drawing Sheets

| LEUPRORELIN OR NAFARELIN NASAL SPRAY INSTRUCTIONS ||
|---|---|
| STEP 1 | Administer 3 puffs per nostril |
| STEP 2 | Wait 10 minutes |
| STEP 3 | Administer 3 puffs per nostril |
| Repeat Steps 1 to 3 in 12 hours ||

FIG. 1

| CYCLE DAY | ORAL MEDICATIONS | | NASAL SPRAY | VAGINAL SUPPOSITORIES | OVULATION TEST |
|---|---|---|---|---|---|
| 3 | 2 Clomiphene tablets | 2 Letrozole tablets | | | |
| 4 | 2 Clomiphene tablets | 2 Letrozole tablets | | | |
| 5 | 2 Clomiphene tablets | 2 Letrozole tablets | | | |
| 6 | 2 Clomiphene tablets | 2 Letrozole tablets | | | |
| 7 | 2 Clomiphene tablets | 2 Letrozole tablets | | | |
| 8 | 2 Clomiphene tablets | | | | |
| 9 | 2 Clomiphene tablets | | | 1 Elagolix tablet | |
| 10 | 2 Clomiphene tablets | | | | |
| 11 | 2 Clomiphene tablets | | | 1 Elagolix tablet | Use Ovulation Test (AM and PM)* |
| 12 | | | Leuprorelin or Nafarelin | | Use Ovulation Test (AM and PM)* |
| 13 | | | Leuprorelin or Nafarelin | | Use Ovulation Test (AM and PM)* |

\* The result of the ovulation test (ovulation predictor kit) should be "negative" on Day 11 of the cycle. The result of the ovulation test should be "positive" after administration of the Lueprorelin nasal spray.

FIG. 2

| LEUPRORELIN OR NAFARELIN NASAL SPRAY INSTRUCTIONS ||
|---|---|
| STEP 1 | Administer 3 puffs per nostril |
| STEP 2 | Wait 10 minutes |
| STEP 3 | Administer 3 puffs per nostril |
| Repeat Steps 1 to 3 in 12 hours ||

FIG. 3

| Day 3 Ⓒ Ⓛ | Day 4 Ⓒ Ⓒ Ⓛ | Day 5 Ⓒ Ⓒ Ⓛ |
|---|---|---|
| Day 6 Ⓒ Ⓛ | Day 7 Ⓒ Ⓒ Ⓛ | Day 8 Ⓒ |
| Day 9 Ⓒ Ⓔ | Day 10 Ⓒ | Day 11 Ⓒ Ⓔ Take Ovulation Tests |
| Day 12 Take Nasal Spray Take Ovulation Tests | Day 13 Take Nasal Spray Take Ovulation Tests | Holder for Nasal Spray, Tests, Medications, Directions |

METHOD AND KIT FOR HOME CONTROLLED OVARIAN STIMULATION FOR IN VITRO FERTILIZATION

CROSS-REFERENCE TO RELATED PATENT APPLICATIONS

This application claims the benefit of priority of under 35 U.S.C. Section 120 of U.S. application Ser. No. 16/674,565, filed Nov. 5, 2019 and under 35 U.S.C. Section 119(e) of U.S. Application No. 62/841,571, filed May 1, 2019, which are incorporated by reference in their entirety.

FIELD OF THE INVENTION

The present invention relates to a home controlled ovarian stimulation method for in vitro fertilization or egg freezing and a home in vitro fertilization (IVF) kit.

BACKGROUND

In vitro fertilization (IVF) is an assisted reproductive technology in which the process of fertilizing an egg cell with a sperm cell occurs outside the body in a laboratory dish. Egg freezing is a process in which the egg cells get frozen without the addition of a sperm cell. To begin the IVF or egg freezing processes; the ovulatory process of the female patient is stimulated to produce one or more eggs. The superovulation process is stimulated via the administration of one or more fertility medications that usually involves injections. The one or more eggs are then retrieved from the female patient via a minor surgical procedure called "egg retrieval." If doing IVF, the male partner then provides a sperm sample. The retrieved eggs and the sperm sample are then mixed together in culture media and stored in a laboratory dish to undergo embryo culture (i.e., fertilization of the egg cell by the sperm cell to form an embryo). The embryo culture is then monitored for several days until an embryo has been formed. Once the embryo has formed, it is transferred to a woman's uterus such that it may attach to the uterine lining and begin the pregnancy.

IVF is a common technology used to treat infertility. Egg freezing is a technology to preserve female fertility for future use. However, from the consultation stage to the beginning of pregnancy, IVF or egg freezing can require as many as 9 or more visits to the doctor's offices for the female patient including 4 or more visits over a short period, such as 2 weeks, for monitoring of her hormones (by blood draw) and her follicles where the eggs are (by vaginal ultrasound). Fertility medications for IVF and egg freezing are typically in the form of injections. As such, the IVF and egg freezing processes can be expensive and time-consuming due to the number of doctor's office visits required during the process. More importantly, the intake of daily injectable fertility drugs is uncomfortable and even painful for the majority of the patients due to the number of injections required. In the typical gonadotropin-releasing hormone (GnRH) antagonist IVF protocol, follicle-stimulating hormone (FSH), such as FSH sold under the brand names GONAL-F®, FOLLIS-TIM®, or MENOPUR®, is administered daily by self-injection starting days 1 to 3 of the menstrual cycle for approximately 12 days. On days 7 to 12, a GnRH antagonist, such as ganirelix acetate or cetrotide, is administered daily by self-injection, in addition to the FSH injection. On approximately day 13, the FSH and GnRH antagonist injections are stopped and human chorionic gonadotropin (hCG) and/or leuprolide acetate is administered one time by self-injection to trigger ovulation to get the mature eggs ready for retrieval and fertilization. The patient must self-inject medications at least 19 times in a two-week period.

Accordingly, there is a need for an improved IVF and egg freezing processes that is more cost-effective, less time-consuming, and less painful than conventional IVF and egg freezing processes. These and other needs are addressed by the kit and method of the present application.

BRIEF DESCRIPTION OF THE DRAWINGS

FIG. 1 shows an exemplary medication schedule for a home controlled ovarian hyperstimulation method for IVF/egg freezing in accordance with at least one embodiment herein.

FIG. 2 shows exemplary directions for administration of leuprorelin (leuprolide acetate or nafarelin sold under the brand name SYNAREL®) nasal spray for the home controlled ovarian hyperstimulation method for IVF/egg freezing in accordance with at least one embodiment herein.

FIG. 3 shows the interior of an exemplary supply box of a home IVF kit comprising the medications and tests for the home controlled ovarian hyperstimulation method for IVF/egg freezing in accordance with at least one embodiment herein. Abbreviations: clomiphene citrate tablets ("C"); letrozole tablets ("L"); elagolix vaginal suppository tablets ("E").

DETAILED DESCRIPTION OF CERTAIN EMBODIMENTS

As is well known, the tracking of a woman's menstrual cycle is critical for those who are trying to become pregnant. Most women have a 28-day menstrual cycle. When a woman knows her average menstrual cycle length, she can estimate/predict when she will ovulate. Over the counter "ovulation predictor kits" are used as well to accurately track ovulation. Ovulation happens approximately 14 days before the next period starts. If the average menstrual cycle is 28 days, a woman ovulates around day 14, and the most fertile days are days 12, 13 and 14. As discussed below, the days of the menstrual cycle are tracked and are important in the IVF/egg freezing method of the present invention and therefore, the days discussed below can be tracked using the technique discussed above.

In accordance with one or more embodiments, disclosed herein is a home controlled ovarian hyperstimulation method for IVF/egg freezing. The method provides patients who are struggling with fertility with a home IVF treatment kit and method that limits the number of doctor's office visits, since there is no, or minimal, need to have monitoring with blood and ultrasound. The method does not involve painful injections since the injectables are replaced with pills and nasal spray. The method comprises self-administration of a series of medications by a patient over an 11-day period concluding with the administration of an ovulation test on each of the last 2 days following the 11-day period. The ovulation test is a urine test used to detect luteinizing hormone ("LH") in the urine. At the end of the 11-day process, after the nasal spray inhalation, the results of the urine ovulation test on each of the last 2 days following the 11-day period should be "positive" indicating that the process was successful, and the patient is ready for egg retrieval by a physician. A positive urine ovulation test usually indicates an LH surge, which is usually a level above 15 mIU/mL.

The "start date" for the patient's self-administration of the series of medications over an 11-day period is defined as day 3 of the patient's menstrual cycle. For women who have regular menstrual cycles, which is defined as 28+/−7 days, then day 1 of the patient's menstrual cycle is the first day of the "full flow of blood". In women who skip periods, for example, having one period every 2-6 months, such as women with polycystic ovary syndrome (PCOS), there are two options for determining the start date. In the first option, the patient can start anytime and the first day of medication intake is considered "day 3" of the menstrual cycle. In the second option, the patient's period is induced with progesterone, such as medroxyprogesterone (marketed as Provera®), which is taken for seven days, after which the patient will get a period with day 1 of the patient's menstrual cycle considered to be the first day of the "full flow of blood".

Also disclosed herein in accordance with at least one embodiment is a kit for the home controlled ovarian hyperstimulation method for IVF and egg freezing ("Home IVF Kit"). The kit can comprise a supply box or pouch comprising a series of medications to be taken by the patient over the 11-day period of the method, as well as ovulation tests (ovulation predictor kits) to be utilized at the end of the 11-day period (before and after the nasal spray inhalation). The various medications can be housed in compartments of the supply box or pouch that are labeled by the day in which the particular medication(s) must be self-administered. The kit can also include a medication schedule and directions for self-administration of the various medications and ovulation tests. In certain implementations, the kit can further include replacement medications and/or replacement ovulation tests in case the designated medications/tests for each day of the schedule are lost, misplaced, or damaged.

Also disclosed herein is a home IVF mobile application (mobile app) for use on a patient's mobile device. The mobile app can be configured to allow a patient to perform a number of tasks associated with the home IVF process, including scheduling an initial office visit with a physician, completing evaluation documents for determining whether the patient is a good candidate for home IVF treatments/egg freezing, communicating with the physician via voice, messaging, or video services, and signing medical consent forms.

The referenced home controlled ovarian hyperstimulation method for IVF/egg freezing as well as the home IVF kit are now described more fully with reference to the accompanying drawings, in which one or more illustrated embodiments and/or arrangements are shown. The method and kit of the present application are not limited in any way to the illustrated embodiments and/or arrangements. It should be understood that the method and kit as shown in the accompanying figures are merely exemplary embodiments of the method and kit of the present application, which can be embodied in various forms as appreciated by one skilled in the art. Therefore, it is to be understood that any structural and functional details disclosed herein are not to be interpreted as limiting the method and kit, but rather are provided as a representative embodiment and/or arrangement for teaching one skilled in the art one or more ways to implement the method and the kit.

FIG. 1 displays an exemplary medication schedule for a home controlled ovarian hyperstimulation method for IVF/egg freezing in accordance with one or more embodiments disclosed herein. The IVF/egg freezing method of the present application begins on the start date. On or before the start date, the patient can have an office visit, or video call Skype/Facetime consultation with her physician to discuss the medication schedule and to receive the home IVF kit comprising the various medications and tests. In other implementations, the office visit, or video call consultation will occur weeks or months before the start date and the home IVF kit would be mailed to the patient's home in advance.

Upon receiving the home IVF kit, on the start date, the patient is directed to orally take 50 to 150 mg (one, two, or three 50 mg oral tablets), preferably 100 mg, of clomiphene citrate (marketed as Clomid®) and 2.5 to 7.5 mg, preferably 5 mg, (one, two, or three 2.5 mg oral tablets) of letrozole (marketed as Femara®), instead of the conventional daily injectables. The dose of clomiphene citrate and the dose of letrozole to be given to a specific patient may vary depending on the age, weight, physical condition and responsiveness of the patient to be treated with the doses to be given to the patient determined by the physician. Preferably, when the dose of clomiphene citrate is 50 mg, then the dose of letrozole is 2.5 mg; when the dose of clomiphene citrate is 100 mg, then the dose of letrozole is 5 mg; when the dose of clomiphene citrate is 150 mg, then the dose of letrozole is 7.5 mg. Examples of alternative dosage combinations of clomiphene citrate and letrozole are given in Table 1 below.

TABLE 1

| Clomiphene Citrate (mg) | Letrozole (mg) |
| --- | --- |
| 50 | 2.5 |
| 50 | 5.0 |
| 50 | 7.5 |
| 100 | 2.5 |
| 100 | 5.0 |
| 100 | 7.5 |
| 150 | 2.5 |
| 150 | 5.0 |
| 150 | 7.5 |

Clomiphene citrate is a nonsteroidal, selective estrogen receptor modulator (SERM) that treats infertility in women by stimulating an increase in the amounts of hormones that support the growth and release of a mature egg. Clomiphene citrate has also been used for ovulation induction for decades by fertility specialists. Letrozole is an aromatase inhibitor and thus inhibits the production of estradiol by the ovaries. It has primarily been used to treat certain types of breast cancer in women after menopause or to prevent certain cancers from returning. However, letrozole has also been used for ovulation induction for decades by fertility specialists.

In one or more embodiments, the start date, as defined earlier, will be considered day 3 of the menstrual cycle. On the start date, the patient is directed to take the specified oral doses of clomiphene citrate and letrozole, namely, 50 to 150 mg (one, two, or three 50 mg oral tablets), preferably 100 mg, of clomiphene citrate and 2.5 to 7.5 mg, preferably 5 mg, (one, two, or three 2.5 mg oral tablets) of letrozole, instead of the conventional daily injectables. The patient is then directed to take the same oral dosages of clomiphene citrate and letrozole daily on each of days 4-7, instead of the conventional daily injectables.

On day 8 of the menstrual cycle the patient is directed to orally take only 50 to 150 mg, preferably 100 mg, (one, two, or three 50 mg oral tablets) of clomiphene citrate, and to stop the letrozole.

On day 9 of the menstrual cycle, the patient is directed to orally take 50 to 150 mg, preferably 100 mg, (one, two, or three 50 mg oral tablets) of clomiphene citrate and to either insert vaginally or take orally, depending on the patient's preference, a gonadotropin-releasing hormone (GnRH) antagonist such as elagolix (marketed as ORILISSA®), instead of the expensive injections of ganirelix acetate (GANIRELEX®) or cetrorelix acetate (marketed as CETROTIDE®) used routinely in conventional practices. A dose of 25 mg ($1/8^{th}$ of a pill) up to 200 mg of elagolix (1 full pill), preferably 25 mg, will be used, with the dose being the same whether inserted vaginally or taken orally. Elagolix is a GnRH antagonist that is conventionally used in the treatment of pain associated with endometriosis in women, not for the treatment of infertility. By blocking the GnRH receptor, elagolix suppresses LH release by the pituitary gland and thus prevents LH surge. Ultimately, elagolix suppresses gonadal steroid production, thereby reducing circulating levels of sex hormones such as progesterone, estradiol, and testosterone. Elagolix is generally an oral medication (oral tablet), however in the present method, elagolix is a tablet taken mainly as a vaginal suppository, but may be taken orally based on the patient's preference. Additionally, the lowest and most preferred dose of elagolix (25 mg) that is used is one-eighth of the daily dosage conventionally administered for the treatment of endometriosis (e.g., 200 mg to 400 mg daily). In the method described herein, the lower dose of elagolix taken as a vaginal suppository instead of orally was found to be an effective GnRH antagonist in the patients. Alternative GnRH receptor antagonists that can be used instead of elagolix include linzagolix and relugolix.

On day 10 of the menstrual cycle, the patient is directed to orally take only 50 to 150 mg, preferably 100 mg, (one, two, or three 50 mg oral tablets) of clomiphene citrate.

On day 11 of the cycle, the patient is directed to orally take 100 mg (two 50 mg oral tablets) of clomiphene citrate and to insert vaginally a 25 mg tablet of elagolix as a vaginal suppository, or the elagolix may be taken orally based on the patient's preference. Also, on day 11, the patient is directed to take a home urine ovulation test in the morning (9 am) and in the evening (9 pm). The results of the urine ovulation tests on day 11 should both be negative. A negative urine ovulation test indicates that elagolix is properly suppressing the LH surge from happening. However, if the results of either ovulation test on day 11 is positive, indicating the patient is having a natural LH surge, then the patient should contact her physician to determine whether the patient is already ovulating. If the patient is confirmed to be ovulating at day 11, then the medications for days 12 and 13 discussed below do not need to be administered; and the patient needs to go to the office immediately for the egg retrieval surgical procedure.

On days 12 and 13 of the menstrual cycle, the patient is directed to take doses of leuprorelin (marketed as LUPRON®) dissolved in saline water as a nasal spray (1:20 to 1:40 dilution in saline, which is a total of 30 Units) or nafarelin (marketed as SYNAREL®) prepared by a licensed pharmacist. Leuprorelin is a gonadotrophin-releasing hormone (GnRH) analogue used to treat certain sex hormone-related disorders including breast cancer, prostate cancer, endometriosis, and precocious puberty. Conventionally, leuprorelin is administered as an injection to the muscle or under the skin of the patient. However, in the present method, leuprorelin or nafarelin is administered to the patient as a nasal spray at least once per day, preferably twice a day, and more preferably two times ten minutes apart and then repeated twelve hours later two times ten minutes apart. At least 2 sprays or puffs, preferably 3 sprays or puffs, of the leuprorelin or nafarelin nasal spray are administered in each nostril of the female patient, and, preferably, a second administration of nasal spray is repeated 10 minutes after the first administration. Twelve hours later, at least 2 sprays or puffs, preferably 3 sprays or puffs, of the leuprorelin or nafarelin nasal spray are administered in each nostril of the female patient and, preferably, a second administration of nasal spray is repeated 10 minutes after the first administration. The number of sprays or puffs from the nasal spray given to a specific patient may be adjusted by the physician depending on the age, weight, physical condition and responsiveness of the patient to be treated.

Leuprorelin is available as a leuprolide acetate injection bottle containing 14 mg/2.8 mL). 0.3 mL (30 Units) of the leuprolide acetate is added to 5.7 mL of sterile saline to a sterile nasal spray pump device to produce a 6 mL solution that will produce 120 sprays. Each spray will contain 0.05 mL (6 mL/120 puffs) or 0.25 Units of leuprolide acetate. Patients are instructed to take 3 nasal sprays in each nostril and then 10 minutes later to repeat the three nasal sprays in each nostril. The patient is instructed to repeat this two-step administration of the nasal spray 12 hours later. Nafarelin (marketed as SYNAREL®) is purchased as a concentrated liquid form of 2 mg/mL, with a total volume of 8 mL in the bottle. 1.2 mL from the bottle of nafarelin is added to 6 mL of sterile saline in a sterile nasal pump spray device to make a concentration of 0.4 mg/mL of nafarelin in a total volume of 7.2 mL. Each nasal pump spray device contains approximately 144 sprays. Each spray will contain 0.05 mL of nafarelin (7.2 mL/144 puffs). Patients are instructed to take 3 nasal sprays in each nostril that is repeated in 10 minutes—this will deliver 240 ug of nafarelin. The same dose of two sets of nasal sprays in ten minutes is repeated 12 hours later.

In accordance with one or more embodiments, instructions for the patient for self-administration of the leuprorelin nasal spray is shown in the Table in FIG. 2. As shown in FIG. 2, at the first step, 3 puffs (sprays) of the nasal spray are self-administered by the patient per nostril. After 10 minutes of waiting (second step), the patient then self-administers 3 more puffs (sprays) of the nasal spray per nostril (third step). Twelve hours later, the patient repeats steps 1 to 3. On day 12 of the menstrual cycle, the patient is also directed to take a home urine ovulation test in the morning (9:00 am) and in the evening (9:00 pm). Both ovulation tests should be done before the nasal spray intake and both ovulation test results should be negative. The second administration of the leuprorelin nasal spray (third step) should be done after 9:00 pm. On day 13 of the menstrual cycle, the patient is also directed to take a home urine ovulation test in the morning (9:00 am) and in the evening (9:00 pm). The results of the ovulation tests for the patient should be positive for both ovulation tests, indicating proper intake of the nasal spray as reflected by LH surge, which is responsible for turning the urine ovulation test positive.

If ovulation is not confirmed on day 13 (i.e., results of ovulation tests on day 13 are negative, which are most likely due to improper intake of the nasal spray), then the patient needs to contact the physician immediately, who will most likely ask the patient to retake properly the nasal spray.

If ovulation is confirmed on day 13 (i.e., results of the ovulation tests are positive), then on day 14 the patient makes a visit to the doctor's office for the minor surgical procedure of retrieving the matured egg(s) from the patient. If the patient is doing IVF, not egg freezing, a sperm sample is then mixed together with the retrieved egg(s) in culture media and stored in a laboratory dish to undergo embryo culture. The embryo culture is then monitored for a few days (3-5 days) until one or more embryos has been formed. On day 17 or 19, once the at least one embryo has been formed, it is freshly transferred to the patient's or a women's uterus so that it may attach to the uterine lining and begin the pregnancy. On day 30, the patient can self-administer a home pregnancy test or make a visit to the doctor's office for a beta human chorionic gonadotropin (hCG) blood test to confirm that the patient is pregnant. Another alternative to the freshly transferred embryo(s) would be to do PGT (preimplantation genetic testing) on the embryos then freeze the embryos for future embryo transfer. The PGT is becoming more popular in the United States and other countries and it is well known to lower the risk of miscarriages and improve pregnancy outcome per embryo transfer. It also allows the couple to choose the gender of the embryo.

As mentioned above, the various medications and tests taken by patient on days 3-13 of the patient's menstrual cycle can be provided in a home IVF kit. FIG. 3 shows an exemplary supply box of the kit comprising the medications and tests for the home controlled ovarian hyperstimulation method for IVF/egg freezing in accordance with at least one embodiment herein. As shown in FIG. 3, the supply box can comprise the medications taken by the patent over the 11-day period of the method as discussed above, as well as the ovulation tests (ovulation urine predictor kits) to be utilized at the end of the 11-day period. The various medications can be housed in compartments of the supply box or pouch that are labeled by the day in which the particular medication(s) should be self-administered (i.e., days 3-13) such that the patient does not lose track of the medications she has taken and remembers which medications to take on which days. The kit can also include a medication schedule and directions for self-administration of the various medications (e.g., nasal spray directions, vaginal suppository directions) and the urine ovulation tests. In certain implementations, the kit can further include replacement medications and/or replacement ovulation tests in case the designated medications/tests for each day of the schedule are lost, misplaced, or damaged. As shown in FIG. 3, in an exemplary embodiment of the supply box of the kit, each of days 3-13 has a separate compartment in the box.

As mentioned above, the medications to be taken on the specified days of the cycle can be housed in their respective compartments. For example, as shown in FIG. 3, the medications for day 3, clomiphene citrate tablets (denoted by the "C") and letrozole tablets (denoted by the "L"), are housed in the compartment for day 3 (or start date). Similarly, the medications for day 9, clomiphene citrate tablets and a GnRH antagonist such as elagolix vaginal suppository tablets (denoted by "E"), are housed in the compartment for day 9.

In one or more embodiments, the supply box or pouch can also have a compartment for housing the medication directions and medication schedule. This compartment can also hold the nasal spray and the ovulation tests in embodiments in which the compartments designated for each day are not large enough to hold the nasal spray and/or the ovulation tests. In one or more embodiments, the compartments for each day can also include reminders for the medication regimen of that particular day. For example, as shown in FIG. 3, the compartment for day 11 includes a reminder to the take the ovulation tests. Similarly, as shown in FIG. 3, the compartment for days 12 and 13 can include reminders to take the ovulation tests and the nasal spray. Accordingly, in one or more embodiments, each supply box or pouch can comprise 9-27, preferably 18, 50 mg clomiphene citrate tablets; 5-15, preferably 10, 2.5 mg letrozole tablets; at least one 200 mg elagolix tablet, one leuprorelin or nafarelin nasal spray (comprising at least the amount required for the dosages of day 12), and three ovulation test kits (each having an AM test and a PM test). The supply box or pouch can also include extras doses of one or more of the medications, an extra nasal spray, and/or additional ovulation test kits.

In one embodiment of the kit, the supply box or pouch can comprise nine 50 mg clomiphene citrate tablets, five 2.5 mg letrozole tablets; at least two 25 mg elagolix tablets, one leuprorelin nasal spray (comprising at least the amount required for the dosages of day 12), and three ovulation test kits (each having an AM test and a PM test). In another embodiment of the kit, the supply box or pouch can comprise eighteen 50 mg clomiphene citrate tablets; ten 2.5 mg letrozole tablets; at least two 25 mg elagolix tablets, one leuprorelin nasal spray (comprising at least the amount required for the dosages of day 12), and three ovulation test kits (each having an AM test and a PM test). In another embodiment of the kit, the supply box or pouch can comprise twenty-seven 50 mg clomiphene citrate tablets; fifteen 2.5 mg letrozole tablets; at least two 25 mg elagolix tablets, one leuprorelin nasal spray (comprising at least the amount required for the dosages of day 12), and three ovulation test kits (each having an AM test and a PM test).

As mentioned above, in one or more implementations disclosed herein, the patient can be provided with a home IVF mobile application (mobile app) for use on a patient's mobile device. The mobile app can be configured to allow a patient to perform a number of tasks associated with the IVF process from home, including scheduling office visits with a physician, completing evaluation documents for determining whether the patient is a good candidate for at-home IVF/egg freezing treatments, communicating with the physician via voice, messaging, or video services, and signing medical consent forms. As such, the mobile app allows the patient to avoid making unnecessary trips to the doctor's office. In one or more embodiments, access to the mobile app and directions for utilizing the app can be provided with the home IVF kit.

The home controlled ovarian hyperstimulation method for IVF and egg freezing, as well as the home IVF kit as disclosed herein provide patients with the ability to self-administer IVF/egg freezing medications, thereby limiting the number of office visits that the patient has to make. Further, because the IVF/egg freezing medications are administered in formulations that are not injectables (i.e., oral tablets, vaginal suppositories, nasal sprays), the patient can avoid uncomfortable or painful injections used in traditional IVF/egg freezing medication regimens. Accordingly, the present method and kit provide a convenient, cost-effective, and pain-free medication regimen for patients seeking to achieve pregnancy through IVF/egg freezing.

It should be understood that the IVF/egg freezing method and kit disclosed herein may not be suitable for all patients, and thus should only be undertaken under doctor's supervision and approval.

Example 1

Ganirelex/Cetrotide Injectable Treatments

Five female patients were treated with a GnRH antagonist protocol requiring injections of medications.

One patient, patient no. 1, was injected with 150 Units of FSH on days 3 to 12; half a syringe of 150 mcg/0.5 mL of ganirelix acetate on days 11 and 12; and 50 mg of clomiphene citrate on days 3 to 12; and 2.5 mg of letrozole on days 3 to 7. Luteinizing hormone (LH) blood level was 4.3 mIU/mL on day 10 and dropped to 2 mIU/mL on day 12. These results indicate that the conventional Ganirelex caused a 53.5% drop in LH blood hormone levels.

A second patient, patient no. 2, was injected with 75 Units of FSH on days 4 to 12 and 150 Units on day 13; half a syringe of 150 mcg/0.5 mL of ganirelix acetate on days 11 to 13; 50 mg of clomiphene citrate on days 10 to 12, and 2.5 mg of letrozole on days 3 to 7. Luteinizing hormone (LH) blood level was 12.0 mIU/mL on day 11 and dropped to 6.3 mIU/mL on day 13. These results indicate that the conventional Ganirelex caused a 47.5% drop in LH blood hormone levels.

Three patients, numbered 3 to 5, were injected with 75, 150 and 225 Units of FSH, respectively, on days 4 to 12 and one third a syringe of 150 mcg/0.5 mL of ganirelix acetate on days 11 to 13. Patient no. 3 received 50 mg of clomiphene citrate on days 4 to 12, and 2.5 mg of letrozole on days 4 to 8. Patient no. 4 received 100 mg of clomiphene citrate and 2.5 mg of letrozole on days 4 to 8, and 50 mg of clomiphene citrate on days 9 to 11. Patient no. 5 received no clomiphene citrate or letrozole. Luteinizing hormone (LH) blood level was 12.0, 18.0 and 14.6 mIU/mL, respectively, on day 10 and dropped to 4.9, 16.0 and 14.1 mIU/mL, respectively, on day 12. These results indicate that the conventional Ganirelex caused a drop in LH blood hormone levels of 59.25, 11.1% and 3.4%, respectively.

Example 2

Home Controlled Ovarian Hyperstimulation Method

Five female patients were treated with the controlled ovarian hyperstimulation method described herein using the elagolix pill (vaginal route) instead of the conventional Ganirelex/Cetrotide injectables. On day 3 of the female patient's menstrual cycle, the patient orally took 100 mg (two 50 mg oral tablets) of clomiphene citrate and 5 mg (two 2.5 mg oral tablets) of letrozole. The patient then took the same oral dosages of clomiphene citrate and letrozole daily on each of days 4-7 of the patient's menstrual cycle. On day 8 of the patient's menstrual cycle, the patient orally took only 100 mg (two 50 mg oral tablets) of clomiphene citrate, and stopped the letrozole. On day 9 of the menstrual cycle, the patient orally took 100 mg (two 50 mg oral tablets) of clomiphene citrate and inserted vaginally a 50 mg tablet of elagolix as a vaginal suppository. On day 10 of the menstrual cycle, the patient orally took only 100 mg (two 50 mg oral tablets) of clomiphene citrate. On day 11 of the menstrual cycle, the patient orally took 100 mg (two 50 mg oral tablets) of clomiphene citrate and inserted vaginally a 50 mg tablet of elagolix as a vaginal suppository. Also, on day 11, the patient took a home ovulation test in the morning (9:00 am) and in the evening (9:00 pm). For the patients whose ovulation tests were not positive, then on days 12 and 13, the patient took 2 doses of leuprorelin as a nasal spray (1:40 dilution in saline) as follows. On day 12, after taking a home ovulation test at 9:00 am, 2 puffs (sprays) of the nasal spray were self-administered by the patient per nostril. After 12 hours of waiting, at 9:00 pm the patient took a home urine ovulation test and then self-administered 2 more puffs (sprays) of the nasal spray per nostril. On day 13, the patient repeated the procedure of day 12. Luteinizing hormone (LH) blood level was 7.0 mIU/mL on day 11 and dropped to 1.0 mIU/mL on day 13. These results indicate that the vaginal elagolix caused an 85.7% drop in LH blood hormone levels.

Table 2 below provides a comparison of the efficacy of conventional Ganirelex/Cetrotide injectables treatment for IVF in the five representative patients from Example 1 with the home controlled ovarian hyperstimulation method described herein in the five representative patients from Example 2. As can be seen from the results, the home controlled ovarian hyperstimulation method described herein is more efficacious in suppressing LH blood hormone levels than the traditional Ganirelex/Cetrotide injectables treatment.

TABLE 2

| | LH blood hormone level (mIU/mL) BEFORE medication intake | LH blood hormone level (mIU/mL) AFTER medication intake | % Drop in blood LH hormone level |
| --- | --- | --- | --- |
| Example 1 Conventional Ganielex/Cetrotide Injectables | | | |
| patient 1 | 4.3 | 2.0 | 53.5% |
| patient 2 | 12.0 | 6.3 | 47.5% |
| patient 3 | 12.0 | 4.9 | 59.2% |
| patient 4 | 18.0 | 16.0 | 11.1% |
| patient 5 | 14.6 | 14.1 | 3.4% |
| Example 2 Vaginal elagolix suppository | | | |
| patient 1 | 7.0 | 1.0 | 85.7% |
| patient 2 | 16.7 | 5.7 | 65.9% |
| patient 3 | 10.2 | 3.2 | 68.6% |
| patient 4 | 8.2 | 1.7 | 79.3% |
| patient 5 | 7 | 0.8 | 88.6% |

Although much of the foregoing description has been directed to a home controlled ovarian hyperstimulation method for IVF/egg freezing and a home IVF kit, the method and kit disclosed herein can be similarly deployed and/or implemented in scenarios, situations, and settings far beyond the referenced scenarios. It should be further understood that any such implementation and/or deployment is within the scope of the methods described herein.

It is to be further understood that like numerals/lettering in the drawings represent like elements through the several figures, and that not all components and/or steps described and illustrated with reference to the figures are required for all embodiments or arrangements. Further, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms ""including," "comprising," or "having," "containing," "involving," and variations thereof herein, when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The subject matter described above is provided by way of illustration only and should not be construed as limiting. Various modifications and changes can be made to the subject matter described herein without following the example embodiments and applications illustrated and described, and without departing from the true spirit and scope of the present invention.

Exemplary Methods, Kits and Uses are Set Out in the Following Items

Item 1. A method for home controlled ovarian stimulation in a female patient in preparation for in vitro fertilization (IVF) or egg freezing, the method comprising the steps of:
1) administering one or more clomiphene citrate oral tablets and one or more letrozole oral tablets to the female patient in respective therapeutically effective amounts on each of the days from the start date through day 7 of the female patient's menstrual cycle, wherein the start date is day 3 of the patient's menstrual cycle;
2) administering one or more clomiphene citrate oral tablets to the female patient in a therapeutically effective amount on day 8 of the female patient's menstrual cycle;
3) administering one or more clomiphene citrate oral tablets to the female patient and either inserting vaginally in or administering orally to the female patient a GnRH antagonist in respective therapeutically effective amounts on day 9 of the female patient's menstrual cycle;
4) administering one or more clomiphene citrate oral tablets to the female patient in a therapeutically effective amount on day 10 of the female patient's menstrual cycle;
5) administering one or more clomiphene citrate oral tablets to the female patient and inserting vaginally in or administering orally to the female patient a GnRH antagonist in respective therapeutically effective amounts on day 11 of the female patient's menstrual cycle;
6) testing, on day 11, whether the female patient is ovulating using an ovulation predictor kit, wherein if (a) the testing shows the female patient is ovulating, then no further medications are administered to the female patient, or (b) the testing shows the female patient is not ovulating, then the method proceeds to step 7;
7) administering a leuprorelin or nafarelin nasal spray to the female patient in a therapeutically effective amount one or more times per day on day 12 of the female patient's menstrual cycle; wherein
   a. on day 12, testing whether the female patient is ovulating using an ovulation predictor kit each time before administering the leuprorelin nasal spray to the female patient, wherein if (a) the testing shows the female patient is ovulating, then no further medications are administered to the female patient, or (b) the testing shows the female patient is not ovulating, then the method proceeds to step 8; and
8) administering a leuprorelin or nafarelin nasal spray to the female patient in a therapeutically effective amount one or more times per day on day 13 of the female patient's menstrual cycle; wherein
   a. on day 13, testing whether the female patient is ovulating using an ovulation predictor kit each time before administering the leuprorelin nasal spray to the female patient, wherein if (a) the testing shows the female patient is ovulating, then the controlled ovarian stimulation is successful, or (b) the testing shows the female patient is not ovulating, then the step of administering the leuprorelin nasal spray to the female patient may be repeated.

Item 2. The method of item 1, wherein the therapeutically effective amount of clomiphene citrate is one, two, or three 50 mg oral tablets per day, the therapeutically effective amount of letrozole is one, two, or three 2.5 mg oral tablets per day, the therapeutically effective amount of the GnRH antagonist is 25 to 200 mg per day, wherein the GnRH antagonist is elagolix, and the therapeutically effective amount of leuprorelin or nafarelin nasal spray is three sprays per nostril, wherein each spray contains 0.05 mL of leuprorelin or nafarelin.

Item 3. The method of item 1, wherein the step of administering the leuprorelin nasal spray according to step 7 or step 8 comprises:
   a. administering 3 sprays of the leuprorelin or nafarelin nasal spray in each nostril of the female patient, waiting 10 minutes and repeating administering 3 sprays of the leuprorelin or nafarelin nasal spray in each nostril of the female patient;
   b. waiting approximately 12 hours; and
   c. administering 3 sprays of the leuprorelin or nafarelin nasal spray in each nostril of the female patient, waiting 10 minutes and repeating administering 3 sprays of the leuprorelin or nafarelin nasal spray in each nostril of the female patient.

Item 4. The method of item 1, wherein each ovulation predictor kit comprises two ovulation tests, and wherein the steps of testing whether the patient is ovulating on days 11, 12 or 13 each comprise testing for ovulation in the morning using a first ovulation test and testing for ovulation in the evening using a second ovulation test.

Item 5. A kit for home controlled ovarian stimulation in preparation for in vitro fertilization (IVF) or egg freezing, the kit comprising:
   a supply box or pouch comprising:
   a. a medication schedule and directions for self-administration of various medications;
   b. at least 9 clomiphene citrate oral tablets;
   c. at least 5 letrozole oral tablets;
   d. at least 1 elagolix tablet;
   e. at least 1 leuprorelin or nafarelin nasal spray device pump; and
   f. 3 ovulation test kits each ovulation test kit having 2 ovulation tests.

Item 6. The kit of item 5, wherein the supply box or pouch comprises at least 11 compartments each corresponding to one of 11 days of ovulation treatment in preparation for IVF/egg freezing.

Item 7. The kit of item 5, wherein the clomiphene citrate oral tablets are 50 mg tablets, the letrozole oral tablets are 2.5 mg tablets, the elagolix tablet is a 200 mg tablet, the leuprorelin or nafarelin nasal spray device comprises at least 48 full sprays.

Item 8. The kit of item 5 further comprising a label indicating administration of the 200 mg elagolix tablet in an amount from 25 mg to 200 mg by vaginal insertion or oral administration in a continuing regimen at a frequency of not more than once per day.

Item 9. The kit of item 8, wherein the label indicates administration of the elagolix tablet on day 9 and day 11 of the female patient's menstrual cycle.

Item 10. The kit of item 5 further comprising a label indicating administration of leuprorelin or nafarelin by nasal spray in a continuing regimen at a frequency of at least three sprays per nostril in 12 hour intervals.

Item 11. The kit of item 5, wherein the supply box or pouch comprises 9 clomiphene citrate tablets and 5 letrozole tablets.

Item 12. The kit of item 5, wherein the supply box or pouch comprises 18 clomiphene citrate tablets and 10 letrozole tablets.

Item 13. The kit of item 5, wherein the supply box or pouch comprises 27 clomiphene citrate tablets and 15 letrozole tablets.

Item 14. Clomiphene citrate tablets for use in a method for ovarian stimulation in a female patient in preparation for in vitro fertilization or egg freezing, wherein
  1) one or more clomiphene citrate tablets and one or more letrozole tablets are administered to the female patient in respective therapeutically effective amounts on each of the days from the start date through day 7 of the female patient's menstrual cycle;
  2) one or more clomiphene citrate tablets are administered to the female patient in a therapeutically effective amount on day 8 of the female patient's menstrual cycle;
  3) one or more clomiphene citrate tablets are administered to the female patient and a GnRH antagonist is either inserted vaginally in or is administered orally to the female patient, in respective therapeutically effective amounts on day 9 of the female patient's menstrual cycle;
  4) one or more clomiphene citrate tablets are administered to the female patient in a therapeutically effective amount on day 10 of the female patient's menstrual cycle;
  5) one or more clomiphene citrate tablets are administered to the female patient and a GnRH antagonist is inserted vaginally in or is administered orally to the female patient, in respective therapeutically effective amounts on day 11 of the female patient's menstrual cycle;
  6) on day 11 it is tested, whether the female patient is ovulating using an ovulation predictor kit, wherein if (a) the testing shows the female patient is ovulating, then no further medications are administered to the female patient, or (b) the testing shows the female patient is not ovulating, then
  7) a leuprorelin or nafarelin nasal spray is administered to the female patient in a therapeutically effective amount one or more times per day on day 12 of the female patient's menstrual cycle; wherein
    a. on day 12, it is tested whether the female patient is ovulating using an ovulation predictor kit each time before the leuprorelin or nafarelin nasal spray is administered to the female patient, wherein if (a) the testing shows the female patient is ovulating, then no further medications are administered to the female patient, or (b) the testing shows the female patient is not ovulating, then
  8) a leuprorelin or nafarelin nasal spray is administered to the female patient in a therapeutically effective amount one or more times per day on day 13 of the female patient's menstrual cycle; wherein
    a. on day 13, it is tested whether the female patient is ovulating using an ovulation predictor kit each time before the leuprorelin nasal spray is administered to the female patient, wherein if (a) the testing shows the female patient is ovulating, then the controlled ovarian stimulation is successful, or (b) the testing shows the female patient is not ovulating, then the step of administering the leuprorelin or nafarelin nasal spray to the female patient may be repeated.

Item 15. 1A method for home controlled ovarian stimulation in a female patient in preparation for in vitro fertilization (IVF) or egg freezing, the method comprising the steps of:
  1) administering 150 mg of clomiphene citrate oral tablets and 7.5 mg of letrozole oral tablets to the female patient on each of the days from the start date through day 7 of the female patient's menstrual cycle, wherein the start date is day 3 of the patient's menstrual cycle;
  2) administering 150 mg of clomiphene citrate oral tablets to the female patient on day 8 of the female patient's menstrual cycle;
  3) administering 150 mg of clomiphene citrate oral tablets to the female patient and either inserting vaginally in or administering orally to the female patient a dose of 25 mg of elagolix on day 9 of the female patient's menstrual cycle;
  4) administering 150 mg of clomiphene citrate oral tablets to the female patient on day 10 of the female patient's menstrual cycle;
  5) administering 150 mg of clomiphene citrate oral tablets to the female patient and inserting vaginally in or administering orally to the female patient a patient a dose of 25 mg of elagolix on day 11 of the female patient's menstrual cycle;
  6) testing, on day 11, whether the female patient is ovulating using an ovulation predictor kit, wherein if (a) the testing shows the female patient is ovulating, then no further medications are administered to the female patient, or (b) the testing shows the female patient is not ovulating, then the method proceeds to step 7;
  7) administering, on day 12, 3 sprays of a leuprorelin or nafarelin nasal spray in each nostril of the female patient, waiting 10 minutes and repeating administering 3 sprays of the leuprorelin or nafarelin nasal spray in each nostril of the female patient; waiting approximately 12 hours and administering 3 sprays of the leuprorelin or nafarelin nasal spray in each nostril of the female patient, waiting 10 minutes and repeating administering 3 sprays of the leuprorelin or nafarelin nasal spray in each nostril of the female patient; wherein
    a. on day 12, testing whether the female patient is ovulating using an ovulation predictor kit each time before administering the leuprorelin nasal spray to the female patient, wherein if (a) the testing shows the female patient is ovulating, then no further medications are administered to the female patient, or (b) the testing shows the female patient is not ovulating, then the method proceeds to step 8; and
  8) administering, on day 13, 3 sprays of the leuprorelin or nafarelin nasal spray in each nostril of the female patient, waiting 10 minutes and repeating administering 3 sprays of the leuprorelin or nafarelin nasal spray in each nostril of the female patient; waiting approximately 12 hours and administering 3 sprays of the leuprorelin or nafarelin nasal spray in each nostril of the female patient, waiting 10 minutes and repeating administering 3 sprays of the leuprorelin or nafarelin nasal spray in each nostril of the female patient, wherein on day 13, testing whether the female patient is ovulating using an ovulation predictor kit each time before administering the leuprorelin nasal spray to the female patient, wherein if (a) the testing shows the female patient is ovulating, then the controlled ovarian stimulation is successful, or (b) the testing shows the female patient is not ovulating, then the step of administering the leuprorelin nasal spray to the female patient may be repeated.

Item 16. The method of item 15, wherein the amount of the clomiphene citrate oral tablets in steps 1, 2, 3, 4 and 5 is 100 mg and the amount of the letrozole oral tablets in step 1 is 5 mg.

Item 17. The method of item 15, wherein the amount of the clomiphene citrate oral tablets in steps 1, 2, 3, 4 and 5 is 50 mg and the amount of the letrozole oral tablets in step 1 is 2.5 mg.

What is claimed:

1. A method for home controlled ovarian stimulation in a female patient in preparation for in vitro fertilization (IVF) or egg freezing, the method comprising the steps of:
   1) stimulating an increase in hormones that support growth and release of one or more mature eggs in the female patient;
   2) suppressing luteinizing hormone (LH) release by the pituitary gland by either inserting vaginally in the female patient or administering orally to the female patient a GnRH antagonist in a therapeutically effective amount;
   3) testing whether the female patient is ovulating using an ovulation predictor kit, wherein if (a) the testing shows the female patient is ovulating, then no further medications are administered to the female patient, or (b) the testing shows the female patient is not ovulating, then the method proceeds to step 4;
   4) administering a leuprorelin or nafarelin nasal spray to the female patient, in a therapeutically effective amount one or more times per day for a first day, wherein on the first day of administering the leuprorelin or nafarelin nasal spray to the female patient,
      a. testing whether the female patient is ovulating using an ovulation predictor kit each time before administering the leuprorelin or nafarelin nasal spray to the female patient, wherein if (a) the testing shows the female patient is ovulating, then no further medications are administered to the female patient, or (b) the testing shows the female patient is not ovulating, then the method proceeds to step 5; and
   5) administering a leuprorelin or nafarelin nasal spray to the female patient in a therapeutically effective amount one or more times per day for a second day, wherein on the second day of administering the leuprorelin or nafarelin nasal spray to the female patient,
      a. testing whether the female patient is ovulating using an ovulation predictor kit each time before administering the leuprorelin or nafarelin nasal spray to the female patient, wherein if the testing shows the female patient is ovulating, then the controlled ovarian stimulation is successful.

2. The method of claim 1, wherein the GnRH antagonist is elagolix, linzagolix or relugolix.

3. The method of claim 1, wherein the GnRH antagonist is elagolix.

4. The method of claim 1, wherein the therapeutically effective amount of the GnRH antagonist is 25 to 200 mg per day.

5. The method of claim 1, wherein the therapeutically effective amount of the GnRH antagonist is 25 mg per day.

6. The method of claim 1, wherein the GnRH antagonist is either inserted vaginally in the female patient or administered orally to the female patient on day 9 of the female patient's menstrual cycle.

7. The method of claim 1, wherein the GnRH antagonist is either inserted vaginally in or administered orally to the female patient on day 9 and on day 11 of the female patient's menstrual cycle.

8. The method of claim 1, wherein the therapeutically effective amount of leuprorelin or nafarelin nasal spray is three sprays per nostril, wherein each spray contains 0.05 mL of leuprorelin or nafarelin.

9. The method of claim 1, wherein the step of administering the leuprorelin or nafarelin nasal spray according to step 4 or step 5 comprises:
   a. administering 3 sprays of the leuprorelin or nafarelin nasal spray in each nostril of the female patient, waiting 10 minutes and repeating administering 3 sprays of the leuprorelin or nafarelin nasal spray in each nostril of the female patient;
   b. waiting approximately 12 hours; and
   c. administering 3 sprays of the leuprorelin or nafarelin nasal spray in each nostril of the female patient, waiting 10 minutes and repeating administering 3 sprays of the leuprorelin or nafarelin nasal spray in each nostril of the female patient.

\* \* \* \* \*